US00PP37246P2

(12) United States Plant Patent
van Paassen

(10) Patent No.: US PP37,246 P2
(45) Date of Patent: Feb. 3, 2026

(54) ***ALOE* VERA PLANT NAMED 'SILVERA MOONFIRE'**

(50) Latin Name: *Aloe vera*
Varietal Denomination: SILVERA MOONFIRE

(71) Applicant: Gebr. van Paassen V.O.F., Maasdijk (NL)

(72) Inventor: Sem van Paassen, Maasdijk (NL)

(73) Assignee: Gebr. Van Paassen V.O.F. (NL)

( * ) Notice: Subject to any disclaimer, the term of this patent is extended or adjusted under 35 U.S.C. 154(b) by 0 days.

(21) Appl. No.: 19/179,138

(22) Filed: Apr. 15, 2025

(51) Int. Cl.
*A01H 6/00* (2018.01)
*A01H 5/12* (2018.01)

(52) U.S. Cl.
USPC ..... Plt./373

(58) Field of Classification Search
USPC ..... Plt./373
CPC ..... A01H 6/00; A01H 5/12
See application file for complete search history.

*Primary Examiner* — Keith O. Robinson

(57) ABSTRACT

A new and distinct cultivar of *Aloe vera* plant named 'SILVERA MOONFIRE' is disclosed, characterized by foliage with a dark green background color and a high percentage of light green streaks and overlay. Leaf margins of this new cultivar have either no teeth or very few teeth. The new variety is an *Aloe vera*, typically produced as a garden or container plant.

1 Drawing Sheet

Latin name of the genus and species: *Aloe vera*.
Variety denomination: 'SILVERA MOONFIRE'.

BACKGROUND OF THE INVENTION

The new cultivar is a naturally-occurring whole plant mutation of an unnamed, unpatented *Aloe vera*. 'SILVERA MOONFIRE' was found and selected by the inventor in March 2014 at a nursery in Maasdijk, the Netherlands.

Asexual reproduction of the new cultivar 'SILVERA MOONFIRE' was first performed in Maasdijk, the Netherlands at a commercial greenhouse in September 2024, by basal vegetative cuttings. 'SILVERA MOONFIRE' has since produced several generations and has shown that the unique features of this cultivar are stable and reproduced true to type.

SUMMARY OF THE INVENTION

The cultivar 'SILVERA MOONFIRE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SILVERA MOONFIRE'. These characteristics in combination distinguish 'SILVERA MOONFIRE' as a new and distinct *Aloe* cultivar:

1. Dark green background leaf color with a high percentage cover of light green streaks and overlay color.
2. Leaf margins with either no teeth or very few teeth.

PARENTAL COMPARISON

Plants of the new cultivar 'SILVERA MOONFIRE' are similar to the parental *Aloe vera* in most horticultural characteristics. However, plants of the new variety differ from the parent variety in the following:

1. Leaf color of the new variety is dark green in the background with a very high percentage of light green leaf surface. Leaf color of the parent is dark green with few, small light-green spots.
2. Leaf base of the new variety is wider than the leaf base of the parent.
3. Leaf margins of the new variety has no, or hardly any teeth, while the leaf margins of the parent bears small, few, but regular teeth.
4. Plants of the new variety grow slightly slower and shorter than plants of the parent variety.

COMMERCIAL COMPARISONS

'SILVERA MOONFIRE' can be compared to the unpatented commercial variety *Aloe vera* 'AMIAL2301', unpatented. The two *Aloe* varieties are similar in most horticultural characteristics; however, the new variety differs in the following:

1. Leaf color of the new variety is dark green with a very high percentage of light green leaf surface. Leaf color of this comparator is dark green with many small, light-green spots.
2. Leaf margins of the new variety has no, or hardly any teeth, while the leaf margins of this comparator has clearly visible and regular teeth.
3. Plants of the new variety are larger than plants of this comparator.

'SILVERA MOONFIRE' can be compared to the unpatented, unnamed *Aloe arborescens*, found in commercial production. The plants are similar in most horticultural characteristics; however, the new variety differs in the following:

1. Leaf color of the new variety is dark green with a very high percentage of light-green leaf surface. Leaf color of this comparator is green with few, small white spots.

2. Leaf margins of the new variety has no, or hardly any teeth, while the leaf margins of this comparator has clearly visible and regular teeth.
3. Leaves of the new variety grow more upright, while leaves of this comparator are more spreading with tops bent downward.

BRIEF DESCRIPTION OF THE PHOTOGRAPH

The accompanying photograph illustrates in full color a typical plant of 'SILVERA MOONFIRE' grown in a greenhouse in Maasdijk, the Netherlands. This plant is approximately 10 months old, shown in a 1 gallon container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 2019 edition, except where general terms of ordinary dictionary significance are used. The following observations and measurements describe 'SILVERA MOONFIRE' plants in a glass greenhouse in Maasdijk, the Netherlands. Temperatures ranged from 15° C. to 30° C. during the day, and 10° C. to 15° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Aloe vera* 'SILVERA MOONFIRE'.

Age of the plant described: 6 months.

PROPAGATION

Time to initiate roots: Approximately 25 days at 22° C.

Root description: Few roots; fleshy, thick, moderately freely-branching. Brown in color, not accurately measured with The R.H.S. Chart.

Propagation method: Vegetative divisions or tissue culture.

PLANT

Plant type: Perennial.

Plant shape: Obovate.

Growth habit: Basal rosette.

Container size: 12 cm pots and larger.

Height: Average 24.2 cm to top of foliar plane; no flowering observed.

Plant spread: Average 24.3 cm.

Growth rate: Moderate.

Vigor: Moderate.

Branching characteristics: Leaves in basal rosettes, no main branches or lateral branches present.

FOLIAGE

Leaf:

*Arrangement.*—Single; spirally placed in rosette.

*Quantity.*—Average 11 leaves per rosette.

*Average length.*—24.3 cm.

*Average width.*—5.9 cm.

*Shape of blade.*—Lanceolate.

*Thickness.*—Average 1.4 cm.

*Whole leaf aspect.*—Succulent, upper side slightly concave to near flat, leaves in an average angle of 50° to horizontal, curved upwards: apices in an average angle of 90° to horizonal.

*Apex.*—Long acuminate.

*Base.*—Broad cuneate, decurrent. Decurrent/sheathing, length: Average: 2.7 cm. Decurrent/sheathing, width: Average: 2.3 cm. Decurrent/sheathing, color: Upper side: RHS Greyed-Green 193A; margined Green 137A, edged Greyed-Green 192B. Under side: RHS Greyed-Green; 192C, broadly margined Green 137C, edged Greyed-Green 192B.

*Margin.*—Entire to finely angulate, winged.

*Texture of top surface.*—Glabrous, smooth.

*Texture of bottom surface.*—Glabrous, smooth.

*Pubescence.*—None.

*Rugosity.*—Both sides non-rugose.

*Luster.*—Upper side: Matte. Under side: Matte.

*Color.*—Young foliage upper side: RHS Green 137A, edged Yellow-Green 145B, densely pustulate, visible as lines, following veins but randomly placed on leaf blade, colored Yellow-Green 147C, fading to Greyed-Green 193A towards the base. Young foliage under side: RHS Green 137A, edged Yellow-Green 145B, densely pustulate, visible as lines, following veins but randomly placed on leaf blade, colored Yellow-Green 146D and 147C, fading to Greyed-Green 193A towards the base. Mature foliage upper side: RHS Green 137A, edged Greyed-Green 193A, tinged Greyed-Orange N170A and N170B, leaf densely pustulate, visible as lines, following veins but randomly placed on leaf blade, average length: 2.9 cm (varying between 0.9 cm and 7.2 cm), average diameter: 0.3 cm, colored Yellow-Green 147C, fading Greyed-Green 193A towards the base. Mature foliage under side: RHS Green 137B, edged Greyed-Green 193A, tinged Greyed-Orange N170A and N170B, leaf very densely pustulate, visible as lines, following veins but randomly placed on leaf blade, average length: 3.8 cm (varying between 0.5 cm and 6.5 cm), average diameter: 0.3 cm, colored Yellow-Green 147C, fading to Greyed-Green 192C towards the base.

*Venation.*—Pattern: Parallel. Color, upper side: Veins only visible in pustulate stripes, colored RHS Yellow-Green 144B. Color, under side: Veins only visible in pustulate stripes, colored RHS Yellow-Green 144B to 144C.

FLOWER

Flowering not observed to date.

REPRODUCTIVE ORGANS

Not observed to date.

OTHER CHARACTERISTICS

Seeds and fruits: Not observed to date.

Temperature tolerance: Unknown, at least tolerant to temperatures up to 40° C. USDA zone 10 to 12.

Disease/pest resistance: Neither resistance nor susceptibility to typically diseases and pests of *Aloe vera* has been observed. Typical diseases include stem rot caused by

*Fusarium oxysporum, Aloe* leaf spot disease (*Curvularia lunata*) and foliar black spot diseases caused by the pathogen *Alternaria tenuissima*. Pests of *Aloe* include *Eriophyid* mites and various weevils and beetles in the Curculionidae family.

What is claimed is:

1. A new and distinct cultivar of *Aloe vera* plant named 'SILVERA MOONFIRE' as herein illustrated and described.

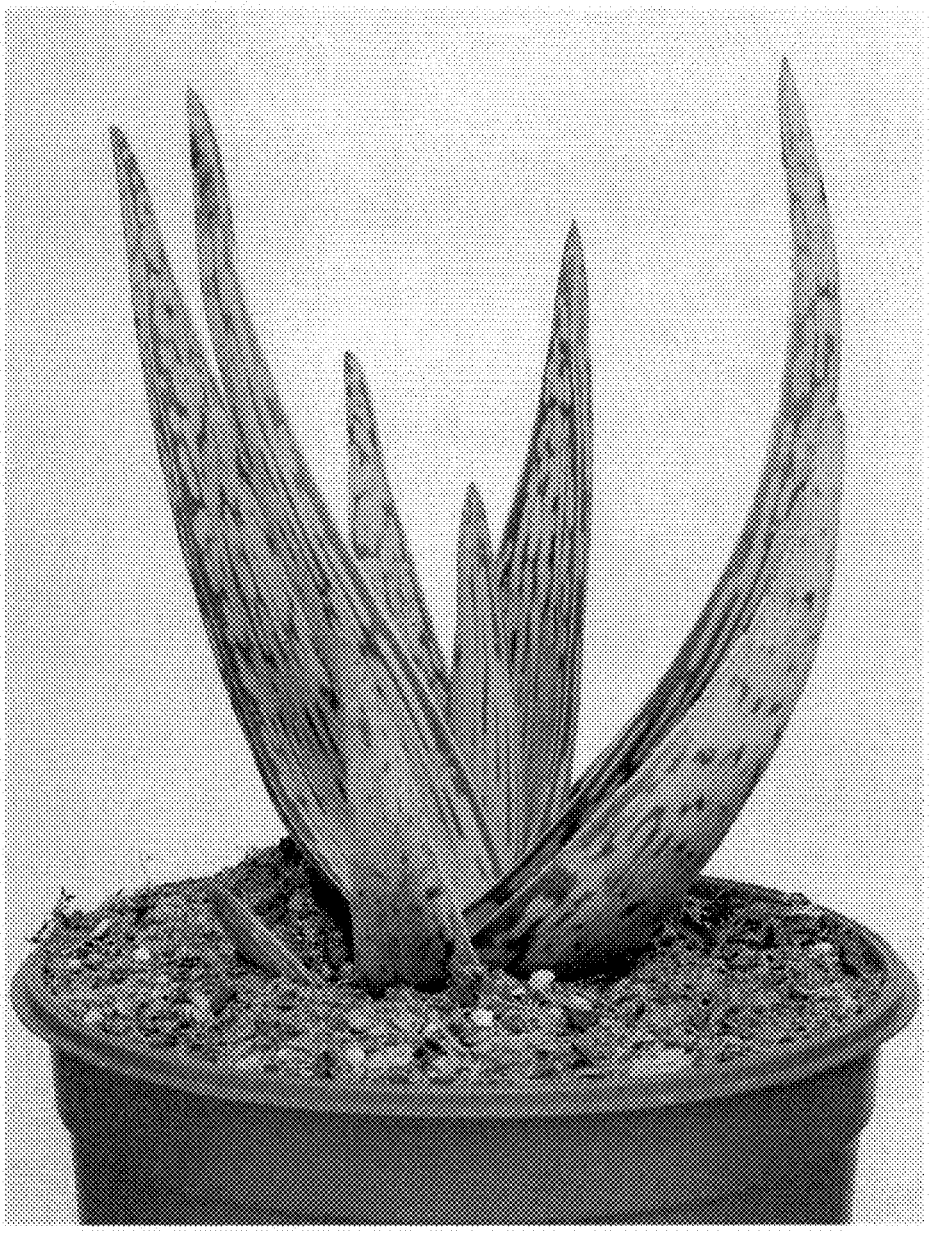

* * * * *